(12) United States Patent
Brazzell et al.

(10) Patent No.: US 9,238,057 B2
(45) Date of Patent: *Jan. 19, 2016

(54) METHOD FOR TREATING OCULAR NEOVASCULARIZATION

(71) Applicant: Novartis AG, Basel (CH)

(72) Inventors: Romulus Kimbro Brazzell, Morrisville, NC (US); Peter Anthony Campochiaro, Baltimore, MD (US); Katharine Hilary Dixon, Olney, MD (US); Michael Kaleko, Rockville, MD (US); Tianci Luo, Clarksville, MD (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/716,925

(22) Filed: Dec. 17, 2012

(65) Prior Publication Data

US 2013/0165503 A1 Jun. 27, 2013

Related U.S. Application Data

(60) Division of application No. 12/785,461, filed on May 23, 2010, now Pat. No. 8,338,384, which is a continuation of application No. 10/080,797, filed on Feb. 21, 2002, now abandoned.

(60) Provisional application No. 60/281,296, filed on Apr. 4, 2001, provisional application No. 60/270,787, filed on Feb. 22, 2001.

(51) Int. Cl.
| | |
|---|---|
| *A61K 48/00* | (2006.01) |
| *A61K 38/39* | (2006.01) |
| *C07K 14/78* | (2006.01) |

(52) U.S. Cl.
CPC ............... *A61K 38/39* (2013.01); *C07K 14/78* (2013.01); *A61K 48/00* (2013.01); *C12N 2799/022* (2013.01); *C12N 2799/027* (2013.01)

(58) Field of Classification Search
CPC .......................... A61K 48/00; C12N 2799/022
See application file for complete search history.

(56) References Cited

U.S. PATENT DOCUMENTS

| | | | |
|---|---|---|---|
| 5,545,423 | A | 8/1996 | Soon-Shiong et al. |
| 5,827,702 | A | 10/1998 | Cuthbertson |
| 5,854,205 | A | 12/1998 | O'Reilly et al. |
| 6,106,826 | A | 8/2000 | Brandt et al. |
| 6,174,861 | B1 | 1/2001 | O'Reilly et al. |
| 6,201,104 | B1 | 3/2001 | MacDonald et al. |
| 6,267,954 | B1 | 7/2001 | Abitbol et al. |
| 6,555,107 | B2 | 4/2003 | Poeschla et al. |
| 6,638,502 | B1 | 10/2003 | Li et al. |
| 6,921,749 | B1 | 7/2005 | Chillemi et al. |
| 7,122,181 | B2 | 10/2006 | Stout et al. |
| 7,125,542 | B2 | 10/2006 | Miller et al. |
| 8,338,384 | B2 | 12/2012 | Brazzell et al. |
| 2002/0086007 | A1 | 7/2002 | Sim et al. |
| 2002/0114783 | A1 | 8/2002 | Appukuttan et al. |
| 2002/0127595 | A1 | 9/2002 | O'Reilly et al. |
| 2003/0082159 | A1 | 5/2003 | Appukuttan et al. |

FOREIGN PATENT DOCUMENTS

| | | |
|---|---|---|
| WO | 94/12161 A1 | 6/1994 |
| WO | 97/15666 A1 | 5/1997 |
| WO | 99/26480 A1 | 6/1999 |
| WO | 00/63249 A1 | 10/2000 |
| WO | 01/58240 A2 | 8/2001 |
| WO | 02/49677 A1 | 6/2002 |
| WO | 2004/027033 A2 | 4/2004 |

OTHER PUBLICATIONS

Ashton, et al., "Intravitreal Delivery of Angistatic Compounds", Investigative Ophthalmology & Visual Science, vol. 39(4):S431 (1998).
Bachelot, et al., "Endonstatin: Preclinical Development as an Anticancer Agent", Curr Med Chem Imun Endoc Metab Agents, vol. 2(4):233-243 (2002).
Berger, et al., "The Angiogenesis Inhibitor, Endostatin, Does Not Affect Murine Cutaneous Wound Healing", Journal of Surgical Research, vol. 91(1):26-31 (2000).
Carmeliet, P., "Angiogenesis in Health and Disease", Nature Med, vol. 9(6):653-660 (2003).
D'Amato, R.J., "Inhibitors of Endothelial Proliferation", Investigative Ophthalmology & Visual Science, vol. 39(4):S431 (1998).
Eberhard, et al., "Heterogeneity of Angiogenesis and Blood Vessel Maturation in Human Tumors: Implications for Antiangiogenic Tumor Therapies", Cancer Res., 60:1388-1393 (2000).
Eder, et al., "Phase I Clinical Trial of Recombinant Human Endostatin Administered as a Short Intravenous Infusion Repeated Daily", Journal of Clinical Oncology, vol. 20(18):3772-3784 (2002).
Eisterer, et al., "Unfulfilled Promise of Endostatin in a Gene Therapy-Xenotransplant Model of Human Acute Lymphocytic Leukemia", Molecular Therapy, vol. 5(4):352-359 (2002).
Hauswirth, W. W., and R.R. McInnes, "Retinal Gene Therapy 1998: Summary of a Workshop", Molecular Vision, 4:11 (1998).
Herbst, et al., "Phase I Study of Recombinant Human Endostatin in Patients with Advanced Solid Tumors", Journal of Clinical Oncology, vol. 20(18):3792-3803 (2002).
Jouanneau, et al., "Lack of Antitumor Activity of Recombinant Endostatin in a Human Neuroblastoma Xenograft Model", Journal of Neuro-Oncology. 51:11-18 (2001).
Keshet, E., and S. A. Ben-Sasson, "Anticancer Drug Targets: Approaching Angiogenesis", The Journal of Clinical Investigation, vol. 104(11):1497-1501 (1999).

(Continued)

*Primary Examiner* — J. E. Angell
(74) *Attorney, Agent, or Firm* — Lewis J. Kreisler

(57) ABSTRACT

Methods are provided for the treatment of ocular neovascularization by increasing, in an individual afflicted with ocular neovascularization, in vivo concentrations of an endostatin protein in the ocular tissues of the individual to an ocular neovascularization inhibiting effective amount, where the endostatin protein has anti-ocular neovascularization activity in vivo.

22 Claims, No Drawings

(56) References Cited

OTHER PUBLICATIONS

King, R.T., "Novel Cancer Approach Stumbles as Others Fail to Repeat Success", Wall Street Journal, Nov. 12, 1998, A1.

King, R.T., and M. Waldholz, "Bristol-Myers Squibb Ends Research on EntreMed's Anticancer Drug", Wall Street Journal, Feb. 10, 1999.

Kulke, et al., "Phase II Study of Recombinant Human Endostatin in Patients with Advanced Neuroendocrine Tumors", Journal of Clinical Oncology, vol. 24(22):3555-3561 (2006).

Kuo, et al., "Comparative Evaluation of the Antitumor Activity of Antiangiogenic Proteins Delivered by Gene Transfer", PNAS, vol. 98(8):4605-4610 (2001).

Kwak, et al., "VEGF is Major Stimulator of Choroidal Neovascularization", Investigative Ophthalmology & Visual Science, vol. 41(10):3158-3164 (2000).

Marshall, E., "Setbacks for Endostatin", Science, vol. 295(5563):2198-2199 (2002).

Mori, et al., "Inhibition of Choroidal Neovascularization by Intravenous Injection of Adenoviral Vectors Expressing Secretable Endostatin", American Journal of Pathology, vol. 159(1):323-320 (2001).

O'Reilly, et al., "Endostatin: An Endogenous Inhibitor of Angiogenesis and Tumor Growth", Cell, vol. 88:277-285 (1997).

Otani, et al., "Expressions of Angiopoietins and Tie2 in Human Choroidal Neovascular Membranes", Investigative Ophthalmology & Visual Science, vol. 40(9):1912-1920 (1999).

Pawliuk, et al, "Continuous Intravascular Secretion of Endostatin in Mice from Transduced Hematopoietic Stem Cells", Molecular Therapy, vol. 5(4):345-351 (2002).

Sauter, et al., "Adenovirus-mediated Gene Transfer of Endostatin in vivo Results in High Level of Transgene Expression and Inhibition of Tumor Growth and Metastases", PNAS. vol. 97(9):4802-4807 (2000).

Seo, et al., "Dramatic Inhibition of Retinal and Choroidal Neovascularization by Oral Administration of Kinase Inhibitor", American Journal of Pathology, vol. 154(6):1743-1753 (1999).

Steele, F.R., "On the Cover: Endostatin Enigma", Molecular Therapy, vol. 5(4) (2002).

Takahashi, et al., "Intraocular Expression of Endostatin Reduces VEGF-induced Retinal Vascular Permeability, Neovascularization, and Retinal Detachment", The FASEB Journal, vol. 17:896-898 (2003).

Wright, A.F., "Gene Therapy for the Eye", British Journal of Ophthalmology, 81:620-623 (1997).

METHOD FOR TREATING OCULAR NEOVASCULARIZATION

FIELD OF THE INVENTION

The present invention relates to a method for the prophylactic and therapeutic treatment of ocular neovascularization. This invention also relates to vectors, more particularly, to retroviral vectors which may be employed in the treatment of ocular neovascularization.

BACKGROUND OF THE INVENTION

Ocular neovascularization has not been successfully treated in the past. Neovascularization of tissues in the front of the eye (i.e. the cornea, iris, and the trabecular meshwork) and other conditions, including conditions in the back of the eye, for example, retinal, subretinal, macular, and optical nerve head neovascularization, can be prevented and treated by application of the methods of the present invention. The methods are useful in preventing and treating ocular neovascularization, including providing for the regression of neovascularization.

SUMMARY OF THE INVENTION

The present invention provides methods for the treatment of ocular neovascularization in an individual comprising effecting an increase, in an individual afflicted with ocular neovascularization, of the in vivo concentration of endostatin in the ocular tissues of the individual to a ocular neovascularization inhibiting effective amount, where endostatin has anti-ocular neovascularization activity in vivo.

In a preferred aspect, endostatin is endostatin or an active fragment of endostatin.

In another preferred aspect, the endostatin employed in the methods of the invention is a polypeptide with the amino acid sequence set forth in SEQ ID NO:1. In another preferred aspect, the endostatin is a polypeptide fragment of the polypeptide with the amino acid sequence set forth in SEQ ID NO:1, a derivative of the polypeptide with the amino acid sequence set forth in SEQ ID NO:1, or a variant of the polypeptide with the amino acid sequence set forth in SEQ ID NO:1. Examples of such active fragments and variants are set forth, e.g., in U.S. Pat. No. 6,174,861, the disclosure of which is incorporated herein in its entirety.

In another preferred aspect, the invention is directed to methods for the treatment of ocular neovascularization in an individual comprising effecting an increase, in an individual afflicted with ocular neovascularization, of the in vivo concentration of endostatin in the ocular tissues of the individual to an ocular neovascularization inhibiting effective amount, where the endostatin has anti-ocular neovascularization activity in vivo, where the increase is effected by administering exogenous endostatin to the individual.

In yet another preferred aspect, the invention is directed to methods for the treatment of ocular neovascularization in an individual comprising effecting an increase, in an individual afflicted with ocular neovascularization, of the in vivo concentration of endostatin in the ocular tissues of the individual to an ocular neovascularization inhibiting effective amount, where endostatin has anti-ocular neovascularization activity in vivo, where the increase is effected by causing endostatin to be produced within the individual. In a more preferred aspect, the increase is effected by administering an effective amount of a viral vector comprising endostatin-encoding nucleic acid to the individual. In a most preferred aspect, the viral vector is selected from the group consisting of an adenovirus, an adeno-associated virus, a retrovirus, and a lentivirus, and is administered intraocularly.

In yet another preferred aspect, the invention is directed to methods for the treatment of ocular neovascularization in an individual comprising effecting an increase, in an individual afflicted with ocular neovascularization, of the in vivo concentration of endostatin in the ocular tissues of the individual to an ocular neovascularization inhibiting effective amount, where endostatin has anti-ocular neovascularization activity in vivo, where the increase is effected by implanting within the individual at least one microcapsule, where the microcapsule comprises cells that secrete endostatin.

DETAILED DESCRIPTION OF THE INVENTION

Endostatin is a cleavage product of collagen type XVIII that has been found to inhibit tumor angiogenesis and growth. Interferon $\alpha 2_a$ also blocks tumor angiogenesis and causes regression of hemangiomas, but has no effect on choroidal neovascularization (CNV). Therefore, inhibitors of tumor angiogenesis do not necessarily inhibit ocular neovascularization. The present invention is predicated on the surprising and unexpected discovery that increasing the in vivo concentration of endostatin in the ocular tissues of the individual to an ocular neovascularization inhibiting effective amount is effective in the treatment of ocular neovascularization.

Accordingly, the present invention provides a method for the prophylactic and therapeutic treatment of ocular neovascularization, e.g., CNV. "Treatment" encompasses both prophylactic and therapeutic treatment. By "prophylactic" is meant the protection, in whole or in part, against ocular neovascularization. By "therapeutic" is meant the amelioration of ocular neovascularization itself, and the protection, in whole or in part, against further ocular neovascularization. The present invention is particularly useful in the treatment of choroidal neovascularization due to macular degeneration, such as age-related macular degeneration. However, the methods of the present invention are also useful in the treatment of other types of ocular neovascularization, including choroidal neovascularizations such as persistent and recurrent choroidal neovascularization, which has been treated, is being treated, or will be treated with laser photocoagulation or photodynamic therapy, and in the treatment of choroidal neovascularization that persists or recurs after surgical removal of an existing choroidal neovascularization.

In addition, the present method is useful in the treatment of choroidal neovascularization due to histoplasmosis and pathological myopia as well as choroidal neovascularization that results from angioid streaks, anterior ischemic optic neuropathy, bacterial endocarditis, Best's disease, birdshot retinochoroidopathy, choroidal hemangioma, choroidal nevi, choroidal nonperfusion, choroidal osteomas, choroidal rupture, choroideremia, chronic retinal detachment, coloboma of the retina, Drusen, endogenous Candida endophthalmitis, extrapapillary hamartomas of the retinal pigmented epithelium, fundus flavimaculatus, idiopathic, macular hole, malignant melanoma, membranproliferative glomerulonephritis (type II), metallic intraocular foreign body, morning glory disc syndrome, multiple evanescent white-dot syndrome (MEWDS), neovascularization at ora serrata, operating microscope burn, optic nerve head pits, photocoagulation, punctate inner choroidopathy, rubella, sarcoidosis, serpiginous or geographic choroiditis, subretinal fluid drainage, tilted disc syndrome, Taxoplasma retinochoroiditis, tuberculosis, or Vogt-Koyanagi-Harada syndrome, among others.

Other types of ocular neovascularization that can be treated with the methods of the present invention are neovascularization due to diabetic retinopathy, non-diabetic retinopathy, branch vein occlusion, central retinal vein occlusion, retinopathy in premature infants, rubeosis iridis, neovascular glaucoma, perifoveal telangiectasis, sickle cell retinopathy, Eale's disease, retinal vasculitis, Von Hippel Lindau disease, radiation retinopathy, retinal cryoinjury, retinitis pigmentosa, retinochoroidal coloboma, corneal neovascularization due to herpes simplex keratitis, corneal ulcers, keratoplasty, pterigyia, or trauma.

The invention is directed to methods for the treatment of ocular neovascularization in an individual afflicted with ocular neovascularization comprising effecting an increase in the amount of an endostatin in ocular tissues of an individual afflicted with ocular neovascularization to an ocular neovascularization inhibiting effective amount.

As used herein, "an ocular neovascularization inhibiting effective amount" of an endostatin is that amount of an endostatin that will cause any or all of: 1) regression of ocular neovascularization (i.e., a decrease in the amount of ocular neovasculature); 2)inhibition of ocular neovascularization; or 3) a decrease in the rate of ocular neovascularization.

The term "DNA sequence encoding endostatin" as used herein means DNA which encodes a full-length endostatin or an active fragment, derivative, or analog of endostatin, e.g., such DNA may be a full-length gene encoding a full-length endostatin, or a truncated gene, or a mutated gene encoding a fragment or derivative or analog of such endostatin which has endostatin activity. The term "DNA sequence" refers generally to a polydeoxyribonucleotide molecule and more specifically to a linear series of deoxyribonucleotides connected one to the other by phosphodiester bonds between the 3' and 5' carbons of the adjacent pentoses.

Thus, in one embodiment, the invention is directed to a DNA sequence that encodes endostatin or a fragment, derivative, or analog thereof having endostatin activity.

DNA sequences encoding endostatin and fragments or derivatives thereof are shown and described in U.S. Pat. No. 5,854,205, which is incorporated by reference herein in its entirety.

The term "endostatin" refers to a protein that is preferably 18 kDa to 20 kDa in size as determined by non-reduced and reduced gel electrophoresis, respectively. The term endostatin also includes active precursor forms of the 18 kDa to 20 kDa protein. The amino acid sequence of full-length human endostatin is set forth in SEQ ID NO:1. The nucleic acid sequence encoding human endostatin is set forth in SEQ ID NO:2. The amino acid sequence of mouse endostatin, plus the mouse Ig kappa leader sequence, is set forth in SEQ ID NO:3. The nucleic acid sequence encoding mouse endostatin with the mouse Ig kappa leader sequence is set forth in SEQ ID NO:4.

The term endostatin also includes fragments of the 18 kDa to 20 kDa protein and modified proteins and peptides that have a substantially similar amino acid sequence, and which are capable inhibiting proliferation of endothelial cells. For example, silent substitutions of amino acids, where the replacement of an amino acid with a structurally or chemically similar amino acid does not significantly alter the structure, conformation or activity of the protein, is well known in the art. Such silent substitutions are intended to fall within the scope of the appended claims.

It will be appreciated that the term "endostatin" includes shortened polypeptides where one or more amino acid is removed from either or both ends of full-length endostatin (i.e., the polypeptide with SEQ ID NO:1), or from an internal region of the protein, yet the resulting molecule remains effective to inhibit endothelial cell proliferation and/or to treat ocular neovascularization. Such shortened polypeptides are referred to herein as "fragments." The term "endostatin" also includes lengthened proteins or peptides where one or more amino acid is added to either or both ends of endostatin, or to an internal location in the protein, yet the resulting molecule retains endothelial proliferation inhibiting activity. Such molecules, for example with tyrosine added in the first position, are useful for labeling, using, e.g., $^{125}$I. Labeling with other radioisotopes may be useful in providing a molecular tool for destroying the target cell containing endostatin receptors. Labeling with "targeting" molecules such as ricin may provide a mechanism for destroying cells with endostatin receptors. Lengthened endostatin polypeptides, or endostatin polypeptides that have been covalently modified, are collectively referred to herein as "derivatives" of endostatin.

"Substantial sequence homology" means at least approximately 70% homology between amino acid residue sequence in the endostatin analog sequence and that of endostatin, preferably at least approximately 80% homology, more preferably at least approximately 90% homology.

Also included in the definition of the term endostatin are modifications of the endostatin protein and its peptide fragments. Such modifications include substitutions of naturally occurring amino acids at specific sites with other molecules, including but not limited to naturally and non-naturally occurring amino acids. Such substitutions may modify the bioactivity of endostatin and produce biological or pharmacological agonists or antagonists. Such modified polypeptides are referred to herein as "variants." Variants, derivatives, and fragments of endostatin that have been shown to have antitumor effects and/or antiangiogenic effects are known and have been reported, e.g., in published international patent application numbers WO0067771, WO0063249, WO9931616, WO9929855, and WO9948924, the disclosures of which are incorporated by reference herein in their entirety. Such variants, derivatives, and fragments of endostatin are also useful in the methods of the present invention.

The polypeptides useful in the practice of the present invention can be delivered to an individual in need of treatment using conventional pharmaceutical formulations.

An additional embodiment of the invention relates to the administration of a pharmaceutical composition, in conjunction with a pharmaceutically acceptable carrier, for any of the therapeutic effects discussed above. Such pharmaceutical compositions may consist of endostatin, e.g., endostatin, or anti-idiotypic antibodies to endostatin, or mimetics of endostatin. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions encompassed by the invention may be administered by any number of routes including, but not limited to, oral, intravenous, intramuscular, intra-articular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated m aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they can be placed in an appropriate container and labeled for treatment of an indicated condition. For administration of endostatin, such labeling would include amount, frequency, and method of administration.

Pharmaceutical compositions suitable for use in the invention include compositions where the active ingredients are contained in an effective amount to achieve the intended purpose. The determination of an effective dose is well within the capability of those skilled in the art.

A therapeutically effective dose of active agent can be estimated initially either in cell culture assays, e.g., of endothelial cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example endostatin or fragments thereof, antibodies to endostatin, agonists, antagonists or inhibitors of endostatin, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts, e.g., when exogenously produced endostatin is administered, may vary from about 0.1 to about 20 mg/kg per day, preferably from 2.5 to 20 mg/kg per day, depending upon the route and method of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc. Various biodegradable and biocompatible polymeric matrices, including microcapsules, nanospheres, and implants, are useful in the practice of the present invention.

Microspheres are fine spherical particles containing active drugs. They are differentiated from nanospheres primarily by the size of the particle; microspheres have a diameter of less than approximately 1000 µm, while nanospheres are submicronic (<1 μm). Microsphere systems contain either homogeneous monolithic microspheres, in which the drug is dissolved or dispersed homogeneously throughout the polymer matrix, or reservoir-type microspheres, in which the drug is surrounded by the polymer matrix membrane shell. Monolithic and reservoir systems can also be combined. For instance, active drug can be dispersed within, or adsorbed onto, the polymer surface in a reservoir-type microsphere.

Biodegradable polymers can consist of either natural or synthetic materials that vary in purity. Natural polymers include polypeptides and proteins (e.g., albumin, fibrinogen, gelatin, collagen), polysaccharides (e.g., hyaluronic acid, starch, chitosan), and virus envelopes and living cells (e.g., erythrocytes, fibroblasts, myoblasts). Natural materials require cross-linking in the microencapsulation process, leading to the denaturation of the polymer and the embedded drug. As a result, synthetic polymers are most commonly used. Frequently used synthetic polymers include poly(-hydroxy) acids such as polylactic acid (PLA), polyhydroxybutryic acid, and copoly (lactic/glycolic) acid (PLGA). These compounds are biocompatible, lack immunogenicity, and have physical properties that permit them to be easily shaped (to control the bioerosion rate).

Colloidal particulate carriers can also be used in the methods of the present invention for delivering endostatin. Liposomes are the preferred colloidal vehicle, and are composed of a phospholipid bilayer that may act as a carrier for both hydrophilic and hydrophobic medications. Liposomes can be made from, e.g., neutral lipids, charged phospholipids, and cholesterol. The addition of an amphophilic polymer such as polyethylene glycol (PEG) onto the surface of a liposome can slow the clearance of liposomes.

Administration of endostatin modified with PEG is also within the scope of the present invention. PEGs are polymers comprised of repeating ethylene oxide subunits with two terminal hydroxyl groups that can be chemically activated. PEG molecules come in a number of different configurations. PEG chains include linear and branched structures in which one or more PEG chains are joined with linkers such as lysine or triazine. PEGs may be attached, preferably covalently, to endostatin at a single site or at multiple sites. Since branched-chain PEGs attach at single or fewer sites than do linear PEGs, branched PEGs may be less likely to interfere with the biologic activity of the native molecule than would the attachment of multiple small linear-chain PEGs, and so are preferred. Pharmaceutical formulations suitable for oral administration of proteins are described, e.g., in U.S. Pat. Nos. 5,008,114; 5,505,962; 5,641,515; 5,681,811; 5,700,486; 5,766,633; 5,792,451; 5,853,748; 5,972,387; 5,976,569; and 6,051,561, all of which are incorporated by reference herein in their entirety.

Endostatin can be delivered to an individual in need of treatment using gene therapy methods. Any of the methods for gene therapy available in the art can be used according to the present invention. Exemplary methods are described below.

In a preferred aspect, the therapeutic comprises endostatin-encoding nucleic acid that is part of an expression vector that expresses endostatin or fragment or chimeric protein thereof in a suitable host. In particular, such a nucleic acid has a promoter operably linked to the polypeptide coding region, the promoter being inducible or constitutive, and, optionally, tissue-specific. In another particular embodiment, a nucleic acid molecule is used in which the polypeptide coding sequences and any other desired sequences are flanked by regions that promote homologous recombination at a desired site in the genome, thus providing for intrachromosomal expression of the desired nucleic acid.

Delivery of endostatin-encoding nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, endostatin-encoding nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see, e.g., U.S. Pat. No. 4,980,286 and others mentioned infra), or by direct injection of naked DNA (see, e.g., Blezinger et al., *Nature Biotechnology*, 17, 343-348 (1999)) or by use of microparticle bombardment (e.g., a gene gun; Biolistic, Dupont), or coating with lipids or cell-surface receptors or transfecting agents, encapsulation in liposomes (see, e.g., Chen et al., *Cancer Research*, 59, 3308-3312 (1999)), microparticles, or microcapsules, or by administering it in linkage to a peptide which is known to enter the nucleus, by administering it in linkage to a ligand subject to receptor-mediated endocytosis (see e.g., U.S. Pat. Nos. 5,166,320; 5,728,399; 5,874,297; and 6,030,954, all of which are incorporated by reference herein in their entirety) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188; and WO 93/20221). Alternatively, the nucleic acid can be introduced intracellularly and incorporated within host cell DNA for expression, by homologous recombination (see, e.g., U.S. Pat. Nos. 5,413,923; 5,416,260; and 5,574,205.

In a specific embodiment, a viral vector that contains endostatin-encoding nucleic acid is used. For example, a retroviral vector can be used (see, e.g., U.S. Pat. Nos. 5,219,740; 5,604,090; and 5,834,182). These retroviral vectors have been modified to delete retroviral sequences that are not necessary for packaging of the viral genome and integration into host cell DNA. Endostatin-encoding nucleic acid to be used in gene therapy is cloned into the vector, which facilitates delivery of the gene into a patient.

Adenoviruses are another type of viral vector that can be used in gene therapy. Adenovirus genomes are linear, double-stranded DNA molecules of approximately 36 kilobase pairs. Each extremity of the viral genome has a short sequence known as the inverted terminal repeat (or ITR), which is necessary for viral replication. The well-characterized molecular genetics of adenovirus render it an advantageous vector for gene transfer. Portions of the viral genome can be substituted with DNA of foreign origin. In addition, recombinant adenoviruses are structurally stable and no rearranged viruses are observed after extensive amplification.

Adenoviruses are especially attractive vehicles for delivering genes to respiratory epithelia. Adenoviruses naturally infect respiratory epithelia where they cause a mild disease. Other targets for adenovirus-based delivery systems are liver cells, the central nervous system, endothelial cells, and muscle. Adenoviruses have the advantage of being capable of infecting non-dividing cells. Methods for conducting adenovirus-based gene therapy are described in, e.g., U.S. Pat. Nos. 5,824,544; 5,868,040; 5,871,722; 5,880,102; 5,882,877; 5,885,808; 5,932,210; 5,981,225; 5,994,106; 5,994,132; 5,994,134; 6,001,557; and 6,033,8843, all of which are incorporated by reference herein in their entirety.

In a specific embodiment, the nucleic acid to be introduced for purposes of gene therapy using an adenoviral vector comprises an inducible promoter operably linked to the coding region, such that expression of the nucleic acid is controllable by controlling the presence or absence of the appropriate inducer of transcription.

The incorporation of genomic elements into the adenoviral vector may provide for enhanced expression of the DNA sequence encoding endostatin. Thus, in accordance with another aspect of the present invention, there is provided an adenoviral vector including at least one DNA sequence encoding a endostatin, and at least one genomic element affecting the expression of such DNA sequence. The term "genomic element" is used as previously defined. Such genomic elements include, but are not limited to, introns, the 5' untranslated region, and the 3' untranslated region, and portions of the introns and 3' and 5' untranslated regions. The adenoviral vector may be as hereinabove described. Promoters which control the DNA sequence may be selected from those described herein and from those known in the art.

The vector, consisting of infectious, but replication-defective, viral particles, which contain at least one DNA sequence encoding endostatin, is administered in vivo to a host in an amount effective to treat choroidal neovascularization in the host. The host may be a mammalian host, including human and non-human primate hosts.

The adenoviral vector may be administered to a mammalian host in an amount effective to provide endostatin levels of up to 1,000,000 ng/ml of blood or 1 mg/ml of blood. Although the adenoviral vector may be administered to a mammalian host in an amount effective to provide endostatin levels of up to 1,000,000 ng/ml, it has been found that some endostatin, such as endostatin, when expressed by mammalian cells transduced with an adenoviral vector of the present invention, is significantly more active (about 1,000 times more active) than endostatin expressed by non-mammalian cells, such as yeast cells or bacterial cells such as E. coli cells. Thus, in order to achieve a desired anti-neovascularization effect, one can generally provide a mammalian host with endostatin at lower levels by administering the adenoviral vector to a mammalian host, as opposed to providing a mammal with significantly greater levels of endostatin expressed by yeast or bacteria.

In one embodiment, when administered to a mammalian host, the adenoviral vector is administered in an amount effective to provide endostatin levels which are from about 2 to 20 times the basal levels of endostatin found in the host. In general, in such an embodiment, the adenoviral vector is administered to a mammalian host in an amount effective to provide for expression of the active polypeptide at a level of at least about 300 ng/ml of blood, preferably from about 300 ng/ml to about 3000 ng/ml, more preferably from about 500 ng/ml to about 1500 ng/ml.

In another embodiment, a viral vector is administered in an amount of from about $10^8$ plaque forming units to about $10^{14}$ plaque forming units, preferably from about $10^8$ plaque forming units to about $10^{11}$ plaque forming units, more preferably from about $10^9$ plaque forming units to about $10^{10}$ plaque forming units. Adenoviral vectors, in the quantities set out above, are preferred.

The infectious vector particles can be administered systemically, such as, for example, by intravenous administration (such as, for example, via peripheral vein injection) or administered via the portal vein, to the bile duct, intramuscularly, intraperitoneally, or intranasally. Alternatively, infectious vector particles can be administered locally, by, e.g, intraocular injection. Such injection can be either into the anterior or posterior chamber of the eye, e.g., into the aqueous humor or vitreous humor. Alternatively, the injection can be subretinal, e.g., by injection of aliquots (e.g., 1 to 10 microliters per aliquot) of vector-containing solution behind the retina, after which the solution is absorbed and the infectious vector particles infect local cells of the ocular tissues and produce the active polypeptide. Such administration can comprise either a single injection, multiple injections administered on the same day, single injections administered over a period of weeks or months, or multiple injections administered over a period of weeks or months.

The vector particles may be administered in combination with a pharmaceutically acceptable carrier suitable for administration to a patient. The carrier may be a liquid carrier (for example, a saline solution), or a solid carrier, such as, for example, mirocarrier beads.

Adeno-associated virus (AAV) has also been proposed for use in gene therapy, including endostatin gene therapy for tumors (see, e.g., Nguyen et al., Cancer Research, 58, 5673-5677 (1998)). Methods for producing and utilizing AAV are described, e.g., in U.S. Pat. Nos. 5,173,414; 5,252,479; 5,552, 311; 5,658,785; 5,763,416; 5,773,289; 5,843,742; 5,869,040; 5,942,496; and 5,948,675, all of which are incorporated by reference herein in their entirety.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny. In another embodiment, an endogenous gene in a cell that is normally not expressed, or expressed at a low level by the cell, can be activated by the operatively linking a strong promoter to the endogenous gene, thus providing a cell that expresses an endogenous gene at high levels, leading to the synthesis and secretion of endostatin by the cell.

Methods for the production and administration of such cells (i.e., those that produce high levels of protein from either endogenous or exogenous genes or nucleic acids) are described in, inter alia, U.S. Pat. Nos. 5,641,670; 5,733,761; 5,968,502; 6,048,729; 6,054,288; 6,063,630; and 6,187,305.

In a preferred embodiment, endostatin-producing cells are delivered in microencapsulated form, e.g., in the form of cells microencapsulated in sodium alginate or calcium alginate poly L-lysine alginate (see, e.g., Read et al., *Nature Biotechnology* 19, 29-34 (January 2001) and Joki et al., *Nature Biotechnology* 19, 35-39 (January 2001)). The microencapsulated cells can be implanted proximally to the eye or at a site where the endostatin produced by the cells will most quickly enter the subject's bloodstream, e.g., in the liver. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, an endostatin-encoding nucleic acid is introduced into the cells such that it is expressible by the cells or their progeny, and the recombinant cells are then administered in vivo for therapeutic effect. In a specific embodiment, stem or progenitor cells are used. Any stem- and/or progenitor cells which can be isolated and maintained in vitro can potentially be used in accordance with this embodiment of the present invention. Such stem cells include but are not limited to hematopoietic stem cells (HSC), stem cells of epithelial tissues such as the skin and the lining of the gut, embryonic heart muscle cells, liver stem cells (see, e.g., WO 94/08598), and neural stem cells.

Epithelial stem cells (ESCs) or keratinocytes can be obtained from tissues such as the skin and the lining of the gut by known procedures. In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture. If the ESCs are provided by a donor, a method for suppression of host versus graft reactivity (e.g., irradiation, drug or antibody administration to promote moderate immunosuppression) can also be used.

With respect to hematopoietic stem cells (HSC), any technique which provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., 1984, J. Clin. Invest. 73:1377-1384). HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91:335) or Witlock-Witte culture techniques (Witlock and Witte, 1982, Proc. Natl. Acad. Sci. USA 79:3608-3612).

The disclosure of all patents, publications, (including published patent applications), and database accession numbers and depository accession numbers referenced in this specification are specifically incorporated herein by reference in their entirety to the same extent as if each such individual patent, publication, and database accession number, and depository accession number are specifically and individually indicated to be incorporated by reference.

It is understood, however, that the scope of the present invention is not to be limited to the specific embodiments described above. The invention may be practiced other than as particularly described and still be within the scope of the accompanying claims.

EXAMPLE 1

Generation of Adenoviral Vectors: Method 1

The mouse endostatin (mEndo) cDNA is amplified by polymerase chain reaction (PCR) from mouse collagen XVIII clone ID 748987 from Genome Systems (St. Louis, Mo.) with the primers 5'-ACT GGT GAC GCG GCC CAT ACT CAT CAG GAC TTT CAG CC-3' (SEQ ID NO:6) and 5'-AAG GGC TAT CGA TCT AGC TGG CAG AGG CCT AT-3' (SEQ ID NO:7) (598-bp F1 fragment). The mouse immunoglobulin k chain leader sequence (Ig-k leader) is PCR amplified from pSecTag2 (InVitrogen, Carlsbad, Calif.) with the primers 5'-CAC TGC TTA CTG GCT TAT CG-3' (SEQ ID NO:8) and 5'-CTG ATG AGT ATG GGC CGC GTC ACC AGT GG-3' (SEQ ID NO:9) (147-bp F2 fragment). PCR is carried out with Pfu DNA polymerase (Stratagene, La Jolla, Calif.) for 35 cycles under the following conditions: 95° C. hot start for 3 min, 95° C. denaturation for 1 min, 55° C. annealing for 1 min, and 72° C. extension for 2 min. The DNA fragments are gel purified. The sig-mEndo chimeric DNA (718 bp) is generated by PCR splice overlap extension with F1 and F2 DNA fragments generated above as templates to assemble mouse Ig-k leader sequence and murine endostatin cDNA. PCR is carried out with the primers 5'-CAC TGC TTA CTG GCT TAT CG-3' (SEQ ID NO:8) and 5'-AAG GGC TAT CGA TCT AGC TGG CAG AGG CCT AT-3' (SEQ ID NO:10), using Pfu DNA polymerase (Stratagene). PCR is run for 35 cycles under the following conditions: 95° C. hot start for 3 min, 95° C. denaturation for 1 min, 60° C. annealing for 1 min, and 72° C. extension for 2 min.

The pAvmEndoLxr adenoviral shuttle plasmid is constructed by inserting the 718-bp sig-mEndo chimeric DNA into the NheI and ClaI sites of adenoviral shuttle plasmid, pAvF9lxr, which is downstream of the Rous sarcoma virus (RSV) promoter and upstream of the simian virus 40 (SV40) polyadenylation signal. An AscI and NheI digested simian cytomegalovirus (sCMV) promoter fragment is substituted for the RSV promoter in pAvmEndoLxc, which is otherwise identical to pAvmEndoLxr. Both shuttle plasmids contain a LoxP site for Cre/lox-mediated recombination. The sequence of the transgenes in the pAvmEndoLxr and pAvmEndoLxc adenoviral plasmids are confirmed by direct sequencing analysis.

Recombinant Av3mEndo (with E1, E2a, and E3 deleted) encoding the sig-mEndo chimera is generated by Cre/lox-mediated recombination of two plasmids, pSQ3 and pAvmEndoLxr. The pSQ3 plasmid contains a loxP site followed by the Av3 genome with the deletion of the region from the left-end inverted terminal repeat (ITR) to the end of E1a. pAvmEndoLxr and pSQ3 are first linearized with NotI and ClaI restriction enzymes, respectively. A transient transfection is performed with 293 cells ($4\times10^5$ cells per well of a six-well plate), using the calcium phosphate mammalian transfection system (Promega, Madison, Wis.). The calcium phosphate-DNA precipitate is prepared with 4.8 mg of linearized pAvmEndoLxr, 12 mg of linearized pSQ3, 6 mg of pcmvCre, and 6 mg of pcmvE2a in a total volume of 1.8 ml. A 0.6-ml calcium phosphate-DNA precipitate is added to each well. The 293 cells are incubated with calcium phosphate-DNA precipitate at 37° C. for 16 hr. The precipitate is removed and the cells are washed with phosphate-buffered saline (PBS). Fifteen days posttransfection, cytopathic effect (CPE) is observed. The cells and the medium are then harvested by scraping. The crude viral lysate is prepared by five cycles of freezing and thawing.

The Av3mEndo vector is reamplified in S8 cells with 0.3 mM dexamethasone in Richter's CM containing 5% FBS until CPE is observed. The adenoviral vector titer (particles per milliliter) and biological titer (plaque-forming units [PFU] per milliliter) are determined as described (Mittereder et al., 1996). Recombinant Av3CsmEndo containing sig-mEndo driven by the CMV promoter is generated in the same manner by Cre/lox-mediated recombination of pSQ3 and pAvmEndoLxc. The correct genome structures of the purified Av3mEndo, Av3CsmEndo, and control Av3Null are confirmed by restriction digests and Southern blot analysis. The Av3mEndo and Av3CsmEndo seedlot are confirmed to be negative for replication-competent adenovirus (RCA).

The supernatant from Av3mEndo-transformed S8 cells contains a 20-kDa protein, the expected size of endostatin, that potently inhibits VEGF165-induced migration of HUVEC cells and ELISA demonstrated that $10^6$ Av3mEndo-transduced Hep3B cells secrete 1-2 µg of murine endostatin per 24 hours.

Generation of Adenoviral Vectors: Method 2

Murine cDNA is obtained by isolating RNA (RNeasy Mini kit; Qiagen, Valencia, Calif.) from snap-frozen 2-week-old C57BL/6 mouse (Charles River Laboratories, Wilmington, Mass.) liver and by treating with Moloney murine leukemia virus reverse transcriptase (Life Technologies, Inc., Gaithersburg, Md.). The murine endostatin gene is cloned into the TA cloning vector (Invitrogen, Carlsbad, Calif.) by PCR using the primers sense 5'-GATCTCTAGACCACCATGCATACT-CATCAGGACTT-3' (SEQ ID NO:11) and antisense 5'-ACTGGAGAAAGAGGTTTATCTAGCTACTAG-3' (SEQ ID NO:12). The 18-amino acid E3/19K signal sequence MRYMILGLLALAAVCSAA (SEQ ID NO:13) is inserted upstream from the endostatin sequence by PCR using the primers sense 5'-GATCTCTAGACCACCATGAGGTACAT-GATTTTAGGCTTGCTCGCCCTTGCGG CAGTCTG-CAGCGCGGCCCATACTCATACTCATCAG-GACTTTCAG-3' (SEQ ID NO:14) and antisense (as above). Plasmid DNA is amplified in DH5 cells (Life Technologies), and the signal sequence-murine endostatin (ss-mEndo) sequence is confirmed (ABI Prism 310 autosequencer; PE Applied Biosystems, Foster City, Calif.).

The ss-mEndo construct is digested with EcoRI and cloned by blunt-end ligation into the multiple cloning site of the adenoviral shuttle plasmid pAd/CMV.1. The resulting plasmid is recombined with type 5 E1A/B-deleted Ad2 and used to infect 293 cells (American Type Culture Collection, Manassas, Va.). Plaque DNA is extracted using proteinase K digestion, phenol extraction, and ethanol precipitation and screened for ss-mEndo by PCR. The resulting virus, Ad-ss-mEndo, is amplified in 293 cells. A similar strategy is used to create control recombinant viruses containing the genes for β-gal (Ad-β-gal) and firefly luciferase (Ad-luc). Viruses are titered using a standard plaque-forming assay in 293 cells. Cells are grown in complete medium consisting of DMEM with 10% FCS, 100 units/ml penicillin, 100 µg/ml streptomycin, 50 µg/ml gentamicin, 0.5 µg/ml Fungizone, and 4 mM glutamine (Biofluids, Rockville, Md.). Cells are infected at MOIs ranging from 0.1 to 100 (105 to 108 pfu per 106 cells in 1.0 ml of complete media) with Ad-ss-mEndo, Ad-luc, or no virus and incubated at 37° C. for 24 h. Supernatants are centrifuged at 2×g for 5 min and assayed for endostatin using a competitive EIA (Cytimmune Sciences, College Park, Md.), according to the manufacturer's instructions. 293 cell supernatants are concentrated 10-fold in cellulose columns (Centricon YM-10; Millipore, Bedford, Mass.) and analyzed by Western blotting (NuPAGE; Novex, San Diego, Calif.) using 570 ng/ml rabbit antimurine endostatin polyclonal IgG antibody (gift of Cytimmune Sciences). The EIA murine endostatin standard is used as a positive control. The susceptibility of the murine colon adenocarcinoma cell line MC38 (developed in the Surgery Branch, National Cancer Institute) to adenoviral infection is tested by infecting cells with Ad-β-gal as described above and assaying for β-gal 24 h later using a staining kit (Boehringer Mannheim, Indianapolis, Ind.). Susceptibility of the murine hepatocyte line NMuLi (American Type Culture Collection) to Ad-β-gal infection is used as a positive control.

Generation of Adenoviral Vectors: Method 3

Liver tissue from a BALB/c mouse is homogenized, and total RNA is extracted (RNeasy kit; Qiagen, Chatsworth, Calif.). First-strand cDNA is amplified by reverse transcription-PCR with oligo(dT) primers (SuperScript II; Life Technologies, Grand Island, N.Y.). The full-length mouse endostatin cDNA is amplified by PCR (sense primer with a ClaI linker, 5'-ATCGATCATACTCATCAG-GACTTTCAGCC-3' (SEQ ID NO:15); antisense primer with a NotI linker, 5'-GCGGCCGCCTATTTGGAGAAAGAG-GTCAT-3' (SEQ ID NO:16) for subcloning into pBluescript (Stratagene). A synthetic oligonucleotide coding for the rat insulin leader sequence is cloned in front of the endostatin gene. After sequence confirmation, the rat insulin leader-endostatin cDNA is cloned into the recombinant adenovirus (ADV) shuttle vector pADV.hEF1-α (human elongation factor 1-α) for the rescue of the recombinant adenovirus as described by Bautista, D. S. et al., (1991) Virology 182, 578-596. The viral particles are measured by absorption (A260), and the plaque-forming units are determined by standard agarose-overlay plaque assay on 293 cells. The cDNA for the construction of the ADV.hVEGF165 is obtained through reverse transcription-PCR of RNA isolated from human umbilical vein endothelial cells (HUVEC). JC and LLC cell lines are obtained from American Type Culture Collection. The cells are cultured in RPMI medium 1640 (JC) and DMEM (LLC). All media are supplemented with 10% FBS, 0.2 mM glutamine, and 1% penicillin/streptomycin. HUVEC are isolated from umbilical cords by collagenase type IV (Sigma) perfusion (0.2% in Hanks' balanced salt solution) for 20 min at room temperature. The cells then are cultured on collagen-coated (1% in PBS) plates in M199 medium supplemented with 20% FBS, 0.2 mM glutamine, 1% penicillin/streptomycin, and 1 ng/ml bFGF.

EXAMPLE 2

Gene Transfer to Mice and Induction of CNV

Viral vectors are injected into the tail vein of adult C57BL/6 mice. Mice are injected with $2\times10^{11}$ particles of either Av3mEndo (n=18) or Av3mNull (n=17) or with $6\times10^{10}$ particles of either Av3CsmEndo or Av3CsNull. Four days after viral vector injection, the mice are anesthetized with ketamine hydrochloride (100 mg/kg body weight), pupils are dilated with 1% tropicamide, and krypton laser photocoagulation is used to rupture Bruch's membrane at 3 locations in each eye of each mouse as previously described by Tobe, et al. Am. J. Pathol. 153, 1641-1646 (1998). Briefly, krypton laser photocoagulation (100 µm spot size, 0.1 seconds duration, 120 mW) is delivered using the slit lamp delivery system of a Coherent Model 920 Photocoagulator and a hand held cover slide as a contact lens. Burns are performed in the 9, 12, and 3 o'clock positions 2-3 disc diameters from the optic nerve. Production of a vaporization bubble at the time of laser, which indicates rupture of Bruch's membrane, is an important factor in obtaining CNV, so only burns in which a bubble is produced are included in the study. A bubble is not produced for 1 burn in mice injected with Av3mEndo and 3 burns in mice injected with Av3mNull. The cornea of one eye of a mouse that had been injected with Av3mEndo has a corneal scar that prevented laser use and that eye is not used.

EXAMPLE 3

Measurement of the Size of Laser-Induced CNV Lesions

Two weeks after laser treatment, the size of CNV lesions is evaluated by one of two different techniques, measurement of the integrated area of CNV on serial sections as previously reported by Seo, et al., Amer. J. Pathol. 154, 1743-1753 (1999) or measurement of the area of CNV in choroidal flat mounts as described by Edelman et al., Invest. Ophthalmol. Vis. Sci. 41, S834 (2000). For mice injected with Av3mEndo, 10 mice are evaluated by the flat mount technique and 8 by serial sections, and for mice injected with Av3mNull, 10 mice are evaluated by the flat mount technique and 7 by serial sections.

Mice used for the flat mount technique are anesthetized and perfused with 1 ml of phosphate-buffered saline containing 50 mg/ml of fluorescein-labeled dextran ($2\times10^6$ average mw, Sigma, St. Louis, Mo.) as previously described by Tobe, et al., Invest. Ophthalmol. Vis. Sci. 39, 180-8 (1998). The eyes are removed and fixed for 1 hour in 10% phosphate-buffered formalin. The cornea and lens are removed and the entire retina is carefully dissected from the eyecup. Radial cuts (4-7, average 5) are made from the edge of the eyecup to the equator and the eyecup is flat mounted in Aquamount with the sclera facing down and the choroid facing up. Flat mounts are examined by fluorescence microscopy and images are digitized using a 3 CCD color video camera and a frame grabber. Image-Pro Plus is used to measure the total area of hyperfluorescence associated with each burn, corresponding to the total fibrovascular scar.

For mice injected with Av3mEndo, a total of 19 eyes are evaluated (one eye had a pre-existent corneal scar that precluded laser treatment) and there is one burn that had not been associated with a bubble, so that 56 lesions are measured. For mice injected with Av3mNull, a total of 20 eyes are evaluated and since there are 3 burns that had not been associated with a bubble, 57 lesions are measured. The areas within each eye are averaged and after log transformation, regression analysis with generalized estimating equations (GEE) is performed. This analysis adjusts for correlation between right and left eyes of each mouse.

Mice used to measure the integrated area of CNV on serial sections are sacrificed 2 weeks after laser treatment and eyes are rapidly removed and frozen in optimum cutting temperature embedding compound (OCT; Miles Diagnostics, Elkhart, Ind.). Frozen serial sections (10 µm) are cut through the entire extent of each burn and histochemically stained with biotinylated griffonia simplicifolia lectin B4 (GSA, Vector Laboratories, Burlingame, Calif.) which selectively binds to vascular cells. Slides are incubated in methanol/$H_2O_2$ for 10 minutes at 4° C., washed with 0.05 M Tris-buffered saline, pH 7.6 (TBS), and incubated for 30 minutes in 10% normal porcine serum. Slides are incubated 2 hours at room temperature with biotinylated GSA and after rinsing with 0.05M TBS, they are incubated with avidin coupled to peroxidase (Vector Laboratories) for 45 minutes at room temperature. After being washed for 10 minutes with 0.05 M TBS, slides are incubated with Histomark Red (Kirkegaard and Perry) to give a red reaction product that is distinguishable from melanin. Some slides are counterstained with Contrast Blue (Kirkegaard and Perry).

To perform quantitative assessments, GSA-stained sections are examined with an Axioskop microscope and images are digitized using a 3 CCD color video camera and a frame grabber. Image-Pro Plus software is used to delineate and measure the area of GSA-stained blood vessels in the subretinal space. For each lesion, area measurements are made for all sections on which some of the lesion appeared and added together to give the integrated area measurement. The measurements within each eye are averaged and regression analysis with GEE is performed.

In initial experiments, the amount of CNV at sites of laser-induced rupture of Bruch's membrane is compared in mice injected with Av3mEndo and mice injected with Av3mNull. The amount of CNV is assessed by two different techniques; measurement of the area of CNV perfused by fluorescein-labeled dextran on choroidal flat mounts and measurement of the area of CNV on serial sections through the entire lesion. The area of laser-induced CNV in choroidal flat mounts appeared less in mice injected with Av3mEndo compared to uninjected mice or mice injected with Av3Null. The difference seen by visual comparison is confirmed by image analysis performed by investigators masked with respect to treatment group, which showed that the mean area of perfused CNV lesions in mice injected with Av3mEndo is significantly less than that in Av3Null-injected controls (Table 1).

TABLE 1

| Area of Perfused CNV on Choriodal Flat Mounts | | | | | |
|---|---|---|---|---|---|
| Vector | Mice | Eyes | Lesions | Area ($10^{-3}$ mm$^2$) | P |
| Av3mEndo | 10 | 19 | 56 | 13.73 ± 1.36 | <0.0001 |
| Av3Null | 10 | 20 | 57 | 29.41 ± 2.19 | |
| Integrated Area of CNV on Serial Sections Through Entire Lesions | | | | | |
| Vector | Mice | Eyes | Lesions | Integrated Area ($10^{-2}$ mm$^2$) | P |
| Av3mEndo | 8 | 15 | 44 | 5.88 ± 0.91 | <0.0001 |
| Av3Null | 7 | 13 | 37 | 12.58 ± 2.21 | |

Serial sectioning through CNV lesions also showed smaller lesions in mice injected with Av3mEndo compared to mice injected with Av3Null. The integrated area of CNV obtained by adding together the area of CNV on each serial section, which assesses size in 3 dimensions, confirmed that there is significantly less CNV at sites of Bruch's membrane rupture in mice injected with Av3mEndo compared to Av3Null injected-mice (Table 1). Since both measurement techniques provide very similar information, only choroidal flat mounts are used in subsequent experiments.

There is an inverse correlation between endostatin serum levels and the area of CNV. Serum levels of endostatin are optimal 4-7 days after intravenous injection of the vectors. A group of mice are injected with Av3mEndo, Av3CsmEndo, Av3Null, or Av3CsNull. Laser treatment is done on day 4 and serum is obtained 7 days after injection. With investigators masked with respect to vector group and endostatin serum level, the area of CNV is measured on choroidal flat mounts 14 days after laser photocoagulation. Mice injected with Av3CsmEndo appear to have less CNV than uninjected mice or those injected with Av3CsNull. Image analysis confirms that the area of CNV lesions is significantly less in mice injected with either Av3CsmEndo or Av3mEndo compared to controls (Table 2).

TABLE 2

Area of Perfused CNV on Choriodal Flat Mounts

| Vector | Mice | Eyes | Lesions | Area ($10^{-3}$ mm$^2$) | P |
|---|---|---|---|---|---|
| Av3CsmEndo | 11 | 22 | 66 | 8.87 ± 0.85 | *<0.0001, **<0.0001 |
| Av3mEndo | 10 | 19 | 55 | 18.36 ± 2.24 | *0.0013, **0.0004 |
| Av3CsNull | 11 | 21 | 62 | 24.41 ± 2.92 | *0.22 |
| Av3Null | 9 | 17 | 48 | 32.91 ± 4.87 | *0.89 |
| No vector | 11 | 21 | 59 | 31.71 ± 3.98 | |

*for difference from no vector controls;
**for difference from coresponding null vector control Plotting the mean area of CNV lesions vs. endostatin serum level in each mouse shows a strong inverse correlation with r=−0.66.

EXAMPLE 4

Analysis of Expression of Endostatin in Eye and Liver

To determine whether systemic administration of adenoviral vectors results in significant transduction of the eye, a group of mice is injected with Av3nBg. This vector expresses β-galactosidase from an RSV promoter. After 5 days, the mice are sacrificed and β-galactosidase activity is measured in homogenates of the eye and liver using a chemiluminescence assay. Livers and eyes are snap frozen following removal from mice. On the day of the assay, livers or eyes are homogenized in lysis buffer (40:1 v/v 1× Reporter Lysis Buffer (Promega, Madison Wis.): Protease Inhibitor Cocktail (Sigma, St Louis Mo.)). Protein content is determined by Bradford Assay (Biorad, Hercules Calif.). β-galactosidase activity is determined using the Galacto-Light system (Tropix, Bedford Mass.).

In the livers of mice that received vector, levels of β-galactosidase activity are approximately 1000-fold higher than uninjected controls, whereas in the eye, the levels of this enzyme activity are similar between vector-injected and control animals. The absence of detectable β-galactosidase activity in the eye following administration of an adenovirus expressing this enzyme suggests that the antiangiogenic effect after intravascular injection of endostatin vectors is due to systemically-produced rather than locally-produced endostatin.

EXAMPLE 5

Comparison of Mice Injected with Av3mEndo to Those Injected with Av3CsmEndo

Mice are injected in the tail vein with $2\times10^{11}$ particles of Av3mEndo (n=10) or Av3mNull (n=9), or they are injected with $6\times10^{10}$ particles of Av3CsmEndo (n=11) or Av3CsmNull (n=11). A no injection control group (n=11) is also included. Four days after injection, Bruch's membrane is ruptured with laser in three places in each eye of each mouse as described above. Seven days after injection, blood is drawn from the tail vein of each mouse and serum is stored at −80° C. for ELISAs. Eighteen days after injection and 14 days after laser, the area of CNV is assessed on choroidal flat mounts as described above.

Endostatin serum levels are determined with a murine endostatin enzyme-linked immunosorbent assay (ELISA) kit (ACCUCYTE murine endostatin: CytImmune Sciences, College Park, Md.) according to the manufacturer's instructions.

Characterization of the second vector construct, Av3CsmEndo, demonstrated that its intravascular injection results in approximately 10-fold higher maximal endostatin levels compared to levels in mice that are injected with the maximum tolerated dose of Av3mEndo particles ($2\times10^{11}$ pfu). Serum levels of endostatin are significantly higher in the Av3mEndo and Av3CsmEndo injected mice than in controls with no injection or a null vector injection. Basal levels of endostatin in mice are found to be between about 30 to 150 ng/ml of serum.

Thus, mice that are injected with a construct in which sig-mEndo expression is driven by the Rous sarcoma virus promoter have moderately high serum levels of endostatin and significantly smaller CNV lesions at sites of laser-induced rupture of Bruch's membrane than mice that are injected with null virus. Mice that are injected with a construct in which sig-mEndo is driven by the simian cytomegalovirus promoter have roughly 10-fold higher endostatin serum levels and have significantly less CNV, with nearly complete inhibition.

EXAMPLE 6

Generation of a Recombinant Adenoviral Vector Encoding Human Endostatin

The human endostatin cDNA is PCR amplified from the cDNA of human α1 (XVIII) collagen. The human liver cDNA is generated from human liver poly A RNA (Clonetech, Palo Alto, Calif.) by reverse transcriptase polymerase chain reaction (RT-PCR). The reverse transcription is carried out with the primer of 5'-TTT TTT TTT CAG TGT AAA AGG TC-3' (SEQ ID NO: 17) using the Perkin Elmer RT-PCR kit (Perkin Elmer Applied Biosystems, Foster City, Calif.) for 1 cycle in the following conditions: room temperature for 10 min, 42° C. reverse transcribing for 3 min, 99° C. denaturation for 5 min, 5° C. cooling for 5 min, and hold at 4° C. until the cDNA is ethanol precipitated and resuspended. The 790 bp human endostatin cDNA fragment is PCR amplified from the prepared cDNA with the primers of 5'-CAG ATG ACA TCC TGG CCA G-3' (SEQ ID NO: 18) and 5'-CTA TAC AGG AAA GTA TGG CAG C-3' (SEQ ID NO: 19). PCR is carried out for 35 cycles in the following condition: 95° C. hot start for 3 min, 80° C. for 3 min followed by the addition of Pfu DNA polymerase (Stratagene, La Jolla, Calif.), 95° C. denaturation for 1 min, 55° C. annealing for 1 min, and 72° C. extension for 3 min. The 790 bp human endostatin cDNA fragment is gel purified and reamplified as described except using the annealing temperature of 58° C. The 790 bp human endostatin cDNA fragment is gel purified and cloned into PCR-Script Amp SK+ using PCR-Script Cloning Kits (Stratagene) according to the manufacturer's procedure to generate perhend 1. The human endostatin cDNA region of the perhend 1 plasmid is confirmed with the direct sequencing analysis by Gene Therapy Core Technologies Molecular Core Laboratory at Genetic Therapy, Inc. Gaithersburg, Md.

The human endostatin cDNA fragment is assembled with human BM40 basement protein leader according to the following procedure. The BM40 basement protein leader is generated by annealing 2 pieces of synthesized oligonucleotides, 5'-GCC AAG CTT CCA TGA GGG CCT GGA TCT TCT TTC TCC TTT GCC TGG CCG GGA GGG CTC TGG CAG CCC CTC AGC AAG AAG CGC TCG CTC ACA GCC ACC GCG ACT TCC AGC CGG TGC TCC A-3' (sense) (SEQ ID NO:20), and 5'-CCA GGT GGA GCA CCG GCT GGA AGT CGC GGT GGC TGT GAG CGA GCG CTT CTT GCT GAG GGG CTG CCA GAG CCC TCC CGG CCA GGC AAA GGA GAA AGA AGA TCC AGG CCC TCA TGG AAG CTT GGC-3' (antisense) (SEQ ID NO:21) followed by Hind III and Sex A1 digestion. The digested BM40 basement protein leader is cloned into Hind III and Sex A1 sites of perhend 1 to generate pBmperhen plasmid. The entire sig-hEndo region of the pBmperhen plasmid is confirmed with the direct sequencing analysis.

The adenovial shuttle plasmid pAV1bmhendlx is generated by substitution of the Factor IX (F9) containing sequence with the sig-Endo containing sequence in pAvF9Lxr adenoviral shuttle plasmid in the following procedure. An 800 bp fragment containing sig-hEndo sequence is generated from pBmperhen by SacI digestion followed by Klenow fill in and Sal I digestion. The pAvF9Lxr plasmid is digested with Bam HI restriction enzyme followed by Klenow fill in and digested with Sal I restriction enzyme to remove F9 containing sequences. The two digested fragments are gel purified and ligated to generate pAV1bmhendlx.

Human endostatin cDNA is RT-PCR generated from the C-terminus of cDNA of human α1 (XVIII) collagen from human liver poly A RNA. The human BM40 basement protein leader is generated from two pieces of synthesized oligonucleotides. The annealed human BM40 basement protein leader is cloned 5' of the human endostatin cDNA to generate sig-hEndo chimeric protein for the secretion of human endostatin protein. The sig-hEndo chimeric DNA is cloned into the adenoviral shuttle plasmid, pAvF9lxr to create pAV1bmhendlx (Figure 12A). The entire sig-hEndo chimeric sequence is confirmed by auto sequencing analysis.

Recombinant Av3bmhendlx (with E1, E2a, and E3-deletions) encoding the sig-hEndo chimeric protein is generated by the "Quick Cre/Lox two plasmid system" according to the following procedure. The plasmids pAV1bmhendlx and pSQ3 are linearized first with Not I and Cla I restriction enzymes, respectively. The S8 cells are pretreated with 0.3 μM dexamethasone 24 hours before the transient transfection that is performed on the 6-well plate at 4×105 S8 cells per well using LipofectAMINE PLUS Reagent (Life Technologies, Rockville, Md.). The lipofectamine complexed DNA is prepared with 1 μg of linearized pSQ3, 0.5 μg pCre, and 0.5 μg linearized pAV1bmhendlx, and 6 μl of lipofectamine according to the manfacturer's procedure (Life Technologies). The S8 cells are incubated with lipofectamine complexed DNA at 37° C. for 4.5 hours. The lipofectamine complexed DNA is removed and the cells are ished with PBS. The transfected S8 cells are cultured at 37° C. with 5% CO2 until the cytopathic effect is observed. The cells and the medium are harvested by scraping. The crude viral lysate is prepared by five cycles of freezing and thawing. The Av3bmhendlx is re-amplified in S8 cells with 0.3 μM dexamethasone in Richter's CM medium containing 5% FBS until cytopathic effect is observed.

Av3bmhendlx-mediated human endostatin expression and secretion is characterized in vector-transduced S8 cells. The supernatant protein of cells infected with Av3bmhendlx, i.e., human endostatin, is analyzed by SDS-PAGE. Each 20 μg of supernatant protein is analyzed on 4 to 12% linear gradient precasted gel. The SDS-PAGE is transferred to a polyvinylidene fluoride membrane. The membrane is stained with Coomassie blue R-250. 20 kDa protein bands, corresponding to the correct size of human endostatin, are excised from a membrane blot and subjected to N-terminal protein sequencing analysis. The protein sequence of three major secreted proteins is determined, with 50% containing the amino acid sequence of human endostatin with the additional amino acid residues APQQEALA (SEQ ID NO: 5), 25% containing residues LA, and 25% containing no residues from human BM40 basement protein signal peptide. The 20 kDa protein is not found in the supernatant protein from Av3NulI cells. The results demonstrate that S8 cells transduced with Av3bmhendlx express and secrete human endostatin after it is processed from human BM40 basement protein signal peptide.

EXAMPLE 7

In vivo Transduction of Retinal Pigment Epithelial Cells with BIV Vectors

Bovine immunodeficiency viral (BIV) vectors encoding eGFP are generated from the three component system (described in published international patent application number WO0144458, the disclosure of which is incorporated by reference herein in its entirety) and are injected into mouse eye via subretinal injection ($5 \times 10^5$ transducing units/per eye). The eye tissue is harvested, sectioned, and examined for eGFP expression at different time points ranging from one week to ten weeks after injection. The sectioned tissue is directly examined by immunofluorescence microscopy for eGFP expression or detected with immunohistochemistry staining. A significant portion of retinal pigment epithelial (RPE) cells are transduced by BIV vectors as indicated by eGFP expression, detected by both immunohistochemical staining and by immunofluorescence.

EXAMPLE 8

Inhibition of Ocular Neovascularization in vivo by BIV Vector Mediated Anti-Angiogenesis Gene Expression A BIV vector encoding murine endostatin prepared according to O'Reilly et al., Cell; 88(2):277-85 (1997) is administered via subretinal injection of transgenic mice (IRBP/rtTA-TRE/VEGF tgMICE) that express Vascular Endothelial Growth Factor from mouse photoreceptor cells upon induction with Doxycyclin. BIV vectors are injected into mouse right eyes while the left eyes serve as controls without injection of vectors. Three weeks after vector injection. 0.5 mg/ml of Doxycyclin is placed in the drinking water for the transgenic mice. It is found that Doxycyclin-induced VEGF expression results in severe neovascularization on the left eyes of the transgenic mice by examination of fluorescein angiograms. VEGF-induced neovascularization is completely blocked by BIV vector-mediated endostatin expression in the right eyes in the same animals.

EXAMPLE 9

Gutless Adenoviral Vector-Mediated Regulated Endostatin Expression in the Eye Results in a Significant Prevention of VEGF-Induced BRB Breakdown in the Mouse Regulated expression of endostatin in vivo using an adenoviral vector delivery system is achieved according to methods described by Xu et al., *Molecular Therapy;* 3:262 (2001). This regulatory system is composed of two components, an inducible transcription factor, and a responsive promoter driving expression of mouse endostatin. The transcription factor consists of a modified human estrogen ligand binding domain that is responsive to tamoxifen, a unique cysteine 2-histidine 2 zinc finger DNA binding motif, and a minimal transactivation domain from VP 16. The responsive promoter consists of 6 repeats of the DNA sequence recognized by the transcription factor DNA binding domain (DBD) and a DNA encoding endostatin. In the presence of tamoxifen, this transcription factor activates transcription from a unique target nucleic acid sequence linked to a minimal promoter. When evaluated with a luciferase reporter in vitro, tamoxifen induces expression up to 250.fold. This system is incorporated into two gutless adenoviral vectors, which are devoid of all viral coding regions. One vector encodes the transcription factor, and the second encodes the target promoter driving transcription of a nucleic acid encoding endostatin. The two vectors are injected into mice, which results in efficient liver transduction. Administration of tamoxifen to the mice results in inducible expression of endostatin, yielding extremely high plasma levels of up to 20 ug/ml. Tamoxifen induction is achieved four times over a two-month period. In the absence of tamoxifen, background levels of endostatin are observed.

This vector system is employed in the mouse eye, using a transgenic mouse model where induction of vascular endothelial growth factor (VEGF) expression causes retinal neovascularization. Specifically, the transgenic mouse (IRBP/rtTA-TRE/VEGF tgMICE) expresses VEGF from mouse photoreceptor cells upon induction with Doxycyclin. 0.5 mg/ml of Doxycyclin is placed in the drinking water for the transgenic mice. Doxycyclin-induced VEGF expression results in severe neovascularization in the control eyes of the transgenic mice that are treated with a gutless adenoviral vector that does not contain a transgene (AGVnull) in the presence of tamoxifen. However, mice that are treated via subretinal injection with a mixture of the two gutless vectors (AGVend) show a significant reduction in BRB breakdown in the presence of tamoxifen. These results demonstrate a significant anti-angiogenic activity of regulated endostatin expression.

What is claimed is:

1. A method for ameliorating or reducing the rate of ocular neovascularization in an individual afflicted with ocular neovascularization, comprising:
   directly administering to the eye or eyes of the individual a replication-defective viral vector that operably encodes and expresses a functionally active endostatin wherein the administering ameliorates or reduces the rate of ocular neovascularization,
   wherein the viral vector is administered to the eye or eyes of the individual intraocularly or subretinally.

2. The method of claim 1, wherein the endostatin is a polypeptide with the amino acid sequence set forth in SEQ ID NO: 1.

3. The method of claim 1, wherein the endostatin is a functionally active polypeptide fragment of the polypeptide with the amino acid sequence set forth in SEQ ID NO:1, a functionally active derivative of the polypeptide with the amino acid sequence set forth in SEQ ID NO:1, or a functionally active variant of the polypeptide with the amino acid sequence set forth in SEQ ID NO: 1.

4. The method of claim 1, wherein endostatin-encoding nucleic acid in the viral vector comprises the sequence set forth in SEQ ID NO:2.

5. The method of claim 1 wherein the ocular neovascularization is caused by a member selected from the group consisting of macular degeneration, histoplasmosis, pathological myopia, angioid streaks, anterior ischemic optic neuropathy, bacterial endocarditis, Best's disease, birdshot retinochoroidopathy, choroidal hemangioma, choroidal nevi, choroidal nonperfusion, choroidal osteomas, choroidal rupture, choroideremia, chronic retinal detachment, coloboma of the retina, Drusen, endogenous *Candida* endophthalmitis, extrapapillary hamartomas of the retinal pigmented epithelium, fundus flavimaculatus, idiopathic, macular hole, malignant melanoma, membranoproliferative glomerulonephritis (type II), metallic intraocular foreign body, morning glory disc syndrome, multiple evanescent white-dot syndrome (MEWDS), neovascularization at ora serrata, operating microscope burn, optic nerve head pits, photocoagulation, punctuate inner choroidopathy, rubella, sarcoidosis, serpiginous or geographic choroiditis, subretinal fluid drainage, tilted disc syndrome, Taxoplasma retinochoroiditis, tuberculosis, Vogt-Koyanagi-Harada syndrome, diabetic retinopathy, non-diabetic retinopathy, branch vein occlusion, central retinal vein occlusion, retinopathy in premature infants, rubeosis iridis, neovascular glaucoma, periofoveal telangiectasis, sickle cell retinopathy, Eale's disease, retinal vasculitis, Von Hippel Linau disease, radiation retinopathy, retinal cryoinjury, retinitis pigmentosa, retinochoroidal coloboma, corneal neovascularization due to herpes simplex keratitis, corneal ulcers, keratoplasty, pterigyia, and trauma.

6. The method of claim 1, wherein the viral vector is an adenoviral vector.

7. The method of claim 1, wherein the viral vector is an adeno-associated viral vector.

8. The method of claim 1, wherein the viral vector is a retroviral vector.

9. The method of claim 1, wherein the ocular neovascularization is retinal neovascularization.

10. The method of claim 1, wherein the ocular neovascularization is corneal neovascularization.

11. The method of claim 1, wherein the ocular neovascularization is iris neovascularization.

12. A method for ameliorating or reducing the rate of ocular choroidal neovascularization in an individual afflicted with ocular choroidal neovascularization, comprising:
    directly administering to the eye or eyes of the individual a replication-defective viral vector that operably encodes and expresses a functionally active endostatin wherein the administering ameliorates or reduces the rate of ocular choroidal neovascularization.

13. The method of claim 12, wherein the endostatin is a polypeptide with the amino acid sequence set forth in SEQ ID NO:1.

14. The method of claim 12, wherein the endostatin is a functionally active polypeptide fragment of the polypeptide with the amino acid sequence set forth in SEQ ID NO:1, a functionally active derivative of the polypeptide with the amino acid sequence set forth in SEQ ID NO:1, or a functionally active variant of the polypeptide with the amino acid sequence set forth in SEQ ID NO:1.

15. The method of claim 12, wherein endostatin-encoding nucleic acid in the viral vector comprises the sequence set forth in SEQ ID NO:2.

16. The method of claim 12, wherein the ocular choroidal neovascularization is caused by a member selected from the group consisting of macular degeneration, histoplasmosis, pathological myopia, angioid streaks, anterior ischemic optic neuropathy, bacterial endocarditis, Best's disease, birdshot retinochoroidopathy, choroidal hemangioma, choroidal nevi, choroidal nonperfusion, choroidal osteomas, choroidal rupture, choroideremia, chronic retinal detachment, coloboma of the retina, Drusen, endogenous *Candida* endophthalmitis, extrapapillary hamartomas of the retinal pigmented epithelium, fundus flavimaculatus, idiopathic, macular hole, malignant melanoma, membranoproliferative glomerulonephritis (type II), metallic intraocular foreign body, morning glory disc syndrome, multiple evanescent white-dot syndrome (MEWDS), neovascularization at ora serrata, operating microscope burn, optic nerve head pits, photocoagulation, punctuate inner choroidopathy, rubella, sarcoidosis, serpiginous or geographic choroiditis, subretinal fluid drainage, tilted disc syndrome, Taxoplasma retinochoroiditis, tuberculosis, Vogt-Koyanagi-Harada syndrome, diabetic retinopathy, non-diabetic retinopathy, branch vein occlusion, central retinal vein occlusion, retinopathy in premature infants, rubeosis iridis, neovascular glaucoma, periofoveal telangiectasis, sickle cell retinopathy, Eale's disease, retinal vasculitis, Von Hippel Linau disease, radiation retinopathy, retinal cryoinjury, retinitis pigmentosa, retinochoroidal coloboma, corneal neovascularization due to herpes simplex keratitis, corneal ulcers, keratoplasty, pterigyia, and trauma.

17. The method according to claim 12, wherein the viral vector is administered intraocularly.

18. The method according to claim 12, wherein the viral vector is administered subretinally.

19. The method according to claim 12, wherein the viral vector is administered intravitreally.

20. The method of claim 12, wherein the viral vector is an adenoviral vector.

21. The method of claim 12, wherein the viral vector is an adeno-associated viral vector.

22. The method of claim 12, wherein the viral vector is a retroviral vector.

* * * * *

SEQUENCE LISTING

```
<160> NUMBER OF SEQ ID NOS: 21

<210> SEQ ID NO 1
<211> LENGTH: 183
<212> TYPE: PRT
<213> ORGANISM: Human

<400> SEQUENCE: 1

His Ser His Arg Asp Phe Gln Pro Val Leu His Leu Val Ala Leu Asn
 1               5                  10                  15

Ser Pro Leu Ser Gly Gly Met Arg Gly Ile Arg Gly Ala Asp Phe Gln
                20                  25                  30

Cys Phe Gln Gln Ala Arg Ala Val Gly Leu Ala Gly Thr Phe Arg Ala
            35                  40                  45

Phe Leu Ser Ser Arg Leu Gln Asp Leu Tyr Ser Ile Val Arg Arg Ala
     50                  55                  60

Asp Arg Ala Ala Val Pro Ile Val Asn Leu Lys Asp Glu Leu Leu Phe
 65                  70                  75                  80

Pro Ser Trp Glu Ala Leu Phe Ser Gly Ser Glu Gly Pro Leu Lys Pro
                 85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
```

```
                   165                 170                 175

Ser Phe Met Thr Ala Ser Lys
                180

<210> SEQ ID NO 2
<211> LENGTH: 551
<212> TYPE: DNA
<213> ORGANISM: Human

<400> SEQUENCE: 2
acagccaccg cgacttccag ccggtgctcc acctggttgc gctcaacagc cccctgtcag      60
gcggcatgcg gggcatccgc ggggccgact tccagtgctt ccagcaggcg cgggccgtgg     120
ggctggcggg caccttccgc gccttcctgt cctcgcgcct gcaggacctg tacagcatcg     180
tgcgccgtgc cgaccgcgca gccgtgccca tcgtcaacct caaggacgag ctgctgtttc     240
ccagctggga ggctctgttc tcaggctctg agggtccgct gaagcccggg gcacgcatct     300
tctcctttga cggcaaggac gtcctgaggc accccacctg ccccagaag agcgtgtggc      360 atggctcgga ccccaacggg cgcaggctga ccgagagcta ctgtgagacg tggcggacgg     420
aggctccctc ggccacgggc caggcctcct cgctgctggg gggcaggctc ctggggcaga     480
gtgccgcgag ctgccatcac gcctacatcg tgctctgcat tgagaacagc ttcatgactg     540
cctccaagta g                                                          551

<210> SEQ ID NO 3
<211> LENGTH: 207
<212> TYPE: PRT
<213> ORGANISM: Mouse

<400> SEQUENCE: 3

Met Glu Thr Asp Thr Leu Leu Leu Trp Val Leu Leu Leu Trp Val Pro
  1               5                  10                  15

Gly Ser Thr Gly Asp Ala Ala His Thr His Gln Asp Phe Gln Pro Val
             20                  25                  30

Leu His Leu Val Ala Leu Asn Thr Pro Leu Ser Gly Gly Met Arg Gly
         35                  40                  45

Ile Arg Gly Ala Asp Phe Gln Cys Phe Gln Gln Ala Arg Ala Val Gly
     50                  55                  60

Leu Ser Gly Thr Phe Arg Ala Phe Leu Ser Ser Arg Leu Gln Asp Leu
 65                  70                  75                  80

Tyr Ser Ile Val Arg Arg Ala Asp Arg Gly Ser Val Pro Ile Val Asn
                 85                  90                  95

Leu Lys Asp Glu Val Leu Ser Pro Ser Trp Asp Ser Leu Phe Ser Gly
            100                 105                 110

Ser Gln Gly Gln Leu Gln Pro Gly Ala Arg Ile Phe Ser Phe Asp Gly
        115                 120                 125

Arg Asp Val Leu Arg His Pro Ala Trp Pro Gln Lys Ser Val Trp His
    130                 135                 140

Gly Ser Asp Pro Ser Gly Arg Arg Leu Met Glu Ser Tyr Cys Glu Thr
145                 150                 155                 160

Trp Arg Thr Glu Thr Thr Gly Ala Thr Gly Gln Ala Ser Ser Leu Leu
                165                 170                 175

Ser Gly Arg Leu Leu Glu Gln Lys Ala Ala Ser Cys His Asn Ser Tyr
            180                 185                 190

Ile Val Leu Cys Ile Glu Asn Ser Phe Met Thr Ser Phe Ser Lys
        195                 200                 205
```

```
<210> SEQ ID NO 4
<211> LENGTH: 624
<212> TYPE: DNA
<213> ORGANISM: Mouse

<400> SEQUENCE: 4
atggagacag acacactcct gctatgggta ctgctgctct gggttccagg ttccactggt      60
gacgcggccc atactcatca ggactttcag ccagtgctcc acctggtggc actgaacacc     120
cccctgtctg gaggcatgcg tggtatccgt ggagcagatt ccagtgcttc cagcaagcc     180 cgagccgtgg ggctgtcggg caccttccgg gctttcctgt cctctaggct gcaggatctc     240
tatagcatcg tgcgccgtgc tgaccggggg tctgtgccca tcgtcaacct gaaggacgag     300
gtgctatctc ccagctggga ctccctgttt tctggctccc agggtcaagt gcaacccggg     360
gcccgcatct tttcttttga cggcagagat gtcctgagac acccagcctg gccgcagaag     420
agcgtatggc acggctcgga ccccagtggg cggaggctga tggagagtta ctgtgagaca     480
tggcgaactg aaactactgg ggctacaggt caggcctcct ccctgctgtc aggcaggctc     540
ctggaacaga aagctgcgag ctgccacaac agctacatcg tcctgtgcat tgagaatagc     600
ttcatgacct ctttctccaa atag                                             624

<210> SEQ ID NO 5
<211> LENGTH: 8
<212> TYPE: PRT
<213> ORGANISM: Human

<400> SEQUENCE: 5

Ala Pro Gln Gln Glu Ala Leu Ala
 1               5

<210> SEQ ID NO 6
<211> LENGTH: 38
<212> TYPE: DNA
<213> ORGANISM: Artificial Sequence
<220> FEATURE:
<223> OTHER INFORMATION: PCR Primer

<400> SEQUENCE: 6
actggtgacg cggcccatac tcatcaggac tttcagcc                              38

<210> SEQ ID NO 7
<211> LENGTH: 32
<212> TYPE: DNA
<213> ORGANISM: Artificial Sequence
<220> FEATURE:
<223> OTHER INFORMATION: PCR Primer

<400> SEQUENCE: 7
aagggctatc gatctagctg gcagaggcct at                                    32

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
cactgcttac tggcttatcg                                                  20
```

<210> SEQ ID NO 9
<211> LENGTH: 29
<212> TYPE: DNA
<213> ORGANISM: Artificial Sequence
<220> FEATURE:
<223> OTHER INFORMATION: PCR Primer

<400> SEQUENCE: 9
ctgatgagta tgggccgcgt caccagtgg                              29

<210> SEQ ID NO 10
<211> LENGTH: 32
<212> TYPE: DNA
<213> ORGANISM: Artificial Sequence
<220> FEATURE:
<223> OTHER INFORMATION: PCR Primer

<400> SEQUENCE: 10
aagggctatc gatctagctg gcagaggcct at                          32

<210> SEQ ID NO 11
<211> LENGTH: 35
<212> TYPE: DNA
<213> ORGANISM: Artificial Sequence
<220> FEATURE:
<223> OTHER INFORMATION: PCR Primer

<400> SEQUENCE: 11
gatctctaga ccaccatgca tactcatcag gactt                       35

<210> SEQ ID NO 12
<211> LENGTH: 30
<212> TYPE: DNA
<213> ORGANISM: Artificial Sequence
<220> FEATURE:
<223> OTHER INFORMATION: PCR Primer

<400> SEQUENCE: 12
actggagaaa gaggtttatc tagctactag                             30

<210> SEQ ID NO 13
<211> LENGTH: 18
<212> TYPE: PRT
<213> ORGANISM: Adenovirus

<400> SEQUENCE: 13

Met Arg Tyr Met Ile Leu Gly Leu Leu Ala Leu Ala Ala Val Cys Ser
 1               5                  10                  15

Ala Ala

<210> SEQ ID NO 14
<211> LENGTH: 96
<212> TYPE: DNA
<213> ORGANISM: Artificial Sequence
<220> FEATURE:
<223> OTHER INFORMATION: PCR Primer

<400> SEQUENCE: 14
gatctctaga ccaccatgag gtacatgatt ttaggcttgc tcgcccttgc ggcagtctgc     60
agcgcggccc atactcatac tcatcaggac tttcag                              96

<210> SEQ ID NO 15
<211> LENGTH: 29
<212> TYPE: DNA
<213> ORGANISM: Artificial Sequence -continued

```
<220> FEATURE:
<223> OTHER INFORMATION: PCR Primer

<400> SEQUENCE: 15
atcgatcata ctcatcagga ctttcagcc                                    29

<210> SEQ ID NO 16
<211> LENGTH: 29
<212> TYPE: DNA
<213> ORGANISM: Artificial Sequence
<220> FEATURE:
<223> OTHER INFORMATION: PCR Primer

<400> SEQUENCE: 16
gcggccgcct atttggagaa agaggtcat                                    29

<210> SEQ ID NO 17
<211> LENGTH: 23
<212> TYPE: DNA
<213> ORGANISM: Artificial Sequence
<220> FEATURE:
<223> OTHER INFORMATION: PCR Primer

<400> SEQUENCE: 17
tttttttttc agtgtaaaag gtc                                          23

<210> SEQ ID NO 18
<211> LENGTH: 19
<212> TYPE: DNA
<213> ORGANISM: Artificial Sequence
<220> FEATURE:
<223> OTHER INFORMATION: PCR Primer

<400> SEQUENCE: 18
cagatgacat cctggccag                                               19

<210> SEQ ID NO 19
<211> LENGTH: 22
<212> TYPE: DNA
<213> ORGANISM: Artificial Sequence
<220> FEATURE:
<223> OTHER INFORMATION: PCR Primer

<400> SEQUENCE: 19
ctatacagga aagtatggca gc                                           22

<210> SEQ ID NO 20
<211> LENGTH: 118
<212> TYPE: DNA
<213> ORGANISM: Artificial Sequence
<220> FEATURE:
<223> OTHER INFORMATION: PCR Primer

<400> SEQUENCE: 20
gccaagcttc catgagggcc tggatcttct ttctcctttg cctggccggg agggctctgg    60
cagcccctca gcaagaagcg ctcgctcaca gccaccgcga cttccagccg gtgctcca     118

<210> SEQ ID NO 21
<211> LENGTH: 123
<212> TYPE: DNA
<213> ORGANISM: Artificial Sequence
<220> FEATURE:
<223> OTHER INFORMATION: PCR Primer

<400> SEQUENCE: 21
```

```
ccaggtggag caccggctgg aagtcgcggt ggctgtgagc gagcgcttct tgctgagggg       60
ctgccagagc cctcccggcc aggcaaagga gaaagaagat ccaggccctc atggaagctt      120
ggc                                                                    123
```